United States Patent [19]

Kagawa et al.

[11] 4,220,592
[45] Sep. 2, 1980

[54] SYNTHESIS OF SUBSTITUTED PHENYLACETIC ACID

[75] Inventors: Keiji Kagawa, Oita; Naoya Kanda, Toyonaka; Fujio Masuko, Ibaraki; Hirotoshi Nakanishi, Minoo, all of Japan

[73] Assignee: Sumitomo Chemical Company, Limited, Osaka, Japan

[21] Appl. No.: 923,351

[22] Filed: Jul. 10, 1978

[30] Foreign Application Priority Data

Jul. 22, 1977 [JP] Japan ................. 52/88743

[51] Int. Cl.$^2$ ............................. C07C 51/08
[52] U.S. Cl. ..................... 260/340.5 R; 562/465; 562/491; 562/496
[58] Field of Search ............... 562/496, 484, 465, 491; 260/340.5 R

[56] References Cited

U.S. PATENT DOCUMENTS 2,489,348  11/1949  Wenner ................. 562/496

FOREIGN PATENT DOCUMENTS 2249880  4/1974  Fed. Rep. of Germany .......... 562/484

Primary Examiner—Jane S. Myers
Attorney, Agent, or Firm—Stevens, Davis, Miller & Mosher

[57] ABSTRACT

A substituted acetonitrile such as α-isopropyl-p-chlorophenylacetonitrile is hydrolyzed using an acid to produce the corresponding substituted phenylacetic acid such as α-isopropyl-p-chlorophenylacetic acid in such a manner that, in a lot in any one hydrolysis reaction, (1) the hydrolysis is carried out in at least two steps, (2) an acid to be used in a subsequent first reaction step is a waste acid produced in a previous second reaction step and the subsequent reaction step(s) thereof if any, and (3) an acid to be used in a second reaction step and the subsequent reaction step(s) if any, is the waste acid produced in a previous second reaction step and subsequent reaction step(s), respectively, and a fresh acid.

7 Claims, No Drawings

SYNTHESIS OF SUBSTITUTED PHENYLACETIC ACID

The present invention relates to an improvement in the process for producing substituted phenylacetic acids by hydrolysis of substituted phenylacetonitriles with an acid.

It is well known that nitriles are converted into the corresponding carboxylic acids by hydrolysis with an acid. For example, the case of α-isopropyl-4-halogenophenylacetic acid is well known in Japanese Patent Application Kokai (Laid-Open) No. 5350/1975.

In producing substituted phenylacetic acids by this process, however, substituted phenylacetic amides produced as an intermediate are liable to remain as impurities in the acids. In order to avoid this, the prior arts need to heat the reaction system at a high temperature for a long time together with a large excess amount of a mineral acid or alkali of high concentration. As a result, various side reactions such as decomposition of the starting materials, decarboxylation of the hydrolyzed products, splitting of substituents and increase of colored components take place at the same time. Further, an excess amount of the hydrolyzing agent needs to be treated after the reaction is finished, and it is not desirable from the standpoints of economy and environmental pollution.

The substituted phenylacetic acids thus produced are very important as intermediates for novel insecticides, medicines and agricultural chemicals. When impurities remain in the acids, consequently, they exert a great adverse effect on the quality and efficacy of the final products.

In order to overcome the drawbacks of the prior art, the present inventors extensively studied a process for producing substituted phenylacetic acids from the corresponding substituted phenylacetonitriles.

The present invention provides a process for hydrolyzing a substituted phenylacetonitrile using an acid to produce the corresponding substituted phenylacetic acid, characterized in that (1) the hydrolysis is carried out in at least two steps, (2) an acid to be used in a first reaction step is a waste acid produced in a second reaction step and if any, subsequent reaction step(s) thereof in a process carried out previously, and (3) an acid to be used in a second reaction step and if any, the subsequent reaction step(s) thereof is a waste acid produced in a second reaction step and subsequent reaction step(s) thereof in a process carried out previously, respectively, and a fresh acid.

According to the process of the present invention, the foregoing drawbacks of the prior art, for example, mass consumption of hydrolyzing agents, environmental pollution owing to an increase in the COD load of waste water, purity-reduction of the products and an increase in manufacturing cost, can be solved; local increase of the amount of acid on reaction becomes possible and therefore shortening of the time required for completion of reaction becomes possible without an increase in acid consumption; and further the operation is easy. As described above, the process of the present invention has great advantages in the commercial production of substituted phenylacetic acids.

The process of the present invention will be first illustrated with reference to the two-step reaction process wherein sulfuric acid is used as the acid.

Nitrile as a starting material (nitrile referred to herein means a substituted phenylacetonitrile; the same applies hereinafter) and a part of a waste acid resulting from the second reaction step described below (referred to as "second waste acid" hereinafter) are supplied to the first reaction step in which the first hydrolysis reaction of nitriles is carried out.

After the first hydrolysis reaction is finished, the reaction mixture is separated into an aqueous layer and oily layer. The aqueous layer, which is a waste acid (referred to as "first waste acid" hereinafter), is discharged from the system, and the oily layer is subjected to the second reaction step.

The remaining part of the second waste acid, a fresh acid and the oil layer obtained in the above first reaction step are mixed to carry out the second hydrolysis reaction. After the second hydrolysis reaction is finished, the reaction mixture is separated into an aqueous layer and oily layer. The aqueous layer is the second waste acid, and the oily layer is the objective carboxylic acid (carboxylic acid referred to herein means a substituted phenylacetic acid; the same applies hereinafter). The second waste acid is circulated to the first and second reaction steps in the following process to be carried out.

The concentration of the acid in each reaction medium of the first and second reaction steps [i.e. the amount of the acid (by weight)×100/the amount of water plus the acid (by weight)] is 60 to 70% by weight.

The amount of the acid used in the first reaction step is fixed within a proper range because it needs to be increased in order to keep the rate of reaction high, while at the same time it needs to be decreased in order to save the acid which results in a decrease in the amount of first waste acid discharged. The amount is generally 0.5 to 3 moles, preferably 0.7 to 2 moles, per mole of the nitrile.

The reaction temperature is not particularly limited, but it is generally within the range of 80° to 250° C. In the reaction under atmospheric pressure, the upper limit of the temperature is nearly the boiling point of the reaction medium. Keeping the reaction system in a liquid form is desirable in terms of the rate of reaction and ease of operation, and therefore when the nitrile as a starting material or the carboxylic acid produced has a high melting point, an organic solvent (e.g. benzene, toluene, xylene, hexane, heptane, chlorobenzene) can be used to dissolve the nitrile and the carboxylic acid, whereby the reaction temperature can be controlled to a desired level. In using the organic solvents, however, problems such as separation, recovery and inflammability of the solvents start to arise. Accordingly, both the first and second reaction steps are preferably carried out without solvent.

Conversion of the nitrile into the carboxylic acid in the first reaction step is fixed within a proper range in order to make the final conversion of the second reaction substantially 100%, to lessen the loss of the acid which is discharged as the first waste acid from the first reaction step, and to shorten the overall reaction time. Consequently, the conversion is fixed to the range of 50 to 95%, preferably 70 to 90%.

The reaction time required for the first reaction step varies with the kind of starting materials, reaction conditions and required conversion, but generally it is about 4 to 6 hours.

After the first hydrolysis reaction is finished, the reaction mixture is separated into an aqueous layer and oily layer. The aqueous layer is discharged from the system as the first waste acid containing ammonium salts dissolved in a high concentration. The oily layer substantially comprises the objective carboxylic acid and substituted phenylacetamide intermediately produced (referred to simply as "amide" hereinafter), and it is supplied to the second reaction step.

The amount of the fresh acid to be supplied to the second reaction step corresponds, in conclusion, to the total of the free acid, the acid consumed to form the salts and water, which are contained in the first waste acid, and water consumed for the hydrolysis. Generally, the amount of the fresh acid is 1 to 3 moles, preferably 1.2 to 2 moles, based on 1 mole of the nitrile supplied to the first reaction step. The concentration of the fresh acid may be substantially 60 to 70%, and the concentration of the second waste acid decreases a little depending upon the degree of conversion in the first reaction step.

To the second reaction step is supplied, in addition to the fresh acid, the second waste acid produced in the second reaction step in the process carried out previously. In this system, the intermediately produced amide which remains in the first reaction step is converted to the carboxylic acid almost completely. The reaction temperature is properly fixed within the same range as in the first reaction step. What is important here is that the total amount of the acids coexisting in the second reaction step is large. The amount of the acid in the second reaction step, which is the total amount of the fresh acid and the waste acid produced in the second reaction in the process carried out previously, can optionally be increased without increasing the acid discharged as the first waste acid, but generally it is 2 to 8 moles, preferably 3 to 5 moles, based on 1 mole of the nitrile supplied to the first reaction step.

The time required for the second reaction step varies depending on the kind of starting materials, reaction conditions and conversion in the first reaction step, but generally it is 2 to 10 hours and the total reaction time through the first and second reaction steps is 6 to 16 hours.

After the second hydrolysis reaction is finished, the reaction mixture is separated into an aqueous layer and oily layer. The aqueous layer is re-used as the second waste acid in the following process to be carried out, and the objective carboxylic acid is obtained as an oily layer at a high purity and in nearly a quantitative yield based on the nitrile.

The carboxylic acid thus obtained may be purified, if necessary, by the usual methods such as washing with water, extraction with solvent, crystallization by cooling, recrystallization and distillation.

The process of the present invention will be explained with reference to the three steps or more (referred to as "multi-step process" hereinafter) wherein sulfuric acid is used as the acid.

The multi-step process corresponds to a process wherein the second reaction step of the foregoing two-step reaction process is carried out in plural steps, and it can be carried out fundamentally in the same manner as in the two-step reaction process. In this case, the supply of fresh acid to every subsequent reaction step(s) after the second reaction step is not necessary, and the supply to at least one step is sufficient. A most commonly employed method is as follows: The waste acid from each subsequent reaction step is reused in each subsequent reaction step in the following process to be carried out; fresh acid is supplied to the final reaction step and a part of the waste acid therefrom is successively supplied, as a substitute for the fresh acid, to the adjacent preceding steps toward the second reaction step, and finally to the second reaction step. The concentration of the acid in the subsequent reaction step(s) is 60 to 70% by weight.

The advantages of the multi-step process consist mainly in that the conversion of nitrile to carboxylic acid at the first reaction step can be fixed at a low level whereby the amount of waste acid discharged from the system can be after all decreased. For this purpose, the three-step reaction process is generally sufficient and the reaction processes having four steps or more have no great significance.

The process of the present invention may be carried out not only as a repeated batchwise process but also as a continuous process. In this case, it is desirable to arrange a plural number of reactors for each reaction step in series so as to inhibit reverse mixing and not to prolong the required retention time.

In the present invention, various modifications can be applied if the requirements of the present invention are satisfied. For example, a small amount of the fresh acid may be added additionally to the first reaction; or the first waste acid may be freed from ammonium salts dissolved therein by aftertreatments such as crystallization and then circulated to the reaction system.

As the acids used in the present invention, any of mineral acids such as sulfuric acid, hydrochloric acid, phosphoric acid, polyphosphoric acid, hydrobromic acid and nitric acid may be used. Most commonly, sulfuric acid is used. These acids may be used alone or in mixtures.

As specific examples of the substituted phenylacetonitrile referred to herein, there may be given α-methylphenylacetonitrile, α-isopropylphenylacetonitrile, α-isopropyl-o, m or p-chlorophenylacetonitrile, α-isopropyl-o, m or p-bromophenylacetonitrile, α-isobutyl-o, m or p-isobutylphenylacetonitrile, α-isopropyl-3,4-methylenedioxyphenylacetonitrile, α-isopropyl-o, m or p-methoxyphenylacetonitrile, α-phenyl-o, m or p-isobutylphenylacetonitrile, α-phenyl-o, m or p-chlorophenylacetonitrile and the like.

As the substituted phenylacetic acids obtained according to the present invention, there may specifically be given the acids corresponding to the foregoing substituted phenylacetonitriles.

The present invention will be illustrated in detail with reference to the following examples, but the present invention is not of course limited to these examples within the scope of the present invention.

EXAMPLE 1

A mixture comprising 320 g of 64.5% sulfuric acid (2.1 moles of 100% sulfuric acid) and 33 g of ammonium bisulfate (0.3 mole) was charged in a 1-liter first reactor equipped with a condenser. 280 g of α-isopropyl-p-chlorophenylacetonitrile (1.5 moles) were added dropwise thereto over a period of more than 3 hours at 142° to 143° C. with stirring, followed by maintaining the same temperature for a further 3 hours. Thus, the first hydrolysis reaction was carried out. The reaction mixture was then separated into an oily layer and aqueous layer.

The yield of the oily layer was 310 g, and the composition of the layer by gas-chromatography was as follows: α-isopropyl-p-chlorophenylacetic acid 80.1%; and α-isopropyl-p-chlorophenylacetamide 19.9%. The yield of the aqueous layer was 320 g, and the composition of the layer by titration analysis was as follows: sulfuric acid 28.4%; and ammonium bisulfate 51.2%.

Next, the oily layer separated was charged in a 2-liter second reactor equipped with a condenser, and 1300 g of 65.0% sulfuric acid (8.7 moles of 100% sulfuric acid) and 100 g of ammonium bisulfate (0.9 mole) were added thereto. The reaction mixture was heated to 144° to 150° C. for 4 hours with stirring. Thus, the second hydrolysis reaction was carried out. The mixture was then separated into an oily layer and an aqueous layer.

The yield of the oily layer was 305 g, and the layer was composed of 100% of the objective α-isopropyl-p-chlorophenylacetic acid (yield: 99.2%). The yield of the aqueous layer was 1400 g, and the layer was composed of 58.4% of sulfuric acid and 9.5% of ammonium bisulfate.

Next, 25% of the aqueous layer from this second reaction step, i.e. 350 g (composition: sulfuric acid 58.4%, ammonium bisulfate 9.5%), was charged in the first reactor for the first hydrolysis reaction in the following process. In the same manner as in the first hydrolysis reaction carried out at first, 280 g of α-isopropyl-p-chlorophenylacetonitrile were added dropwise thereto at 142° to 143° C. with stirring, and the mixture was reacted for a further 6 hours. The yields of the oily layer and aqueous layer were 308 g and 320 g, respectively. The oily layer was composed of 82.5% of α-isopropyl-p-chlorophenylacetic acid and 17.5% of α-isopropyl-p-chlorophenylacetamide. The aqueous layer was composed of 27.6% of sulfuric acid and 52.3% of ammonium bisulfate. This oily layer was charged in the second reactor, and then the rest (75%) of the aqueous layer from the second hydrolysis reaction carried out at first, i.e. 1050 g (composition: sulfuric acid 58.4%, ammonium bisulfate 9.5%), and 350 g of fresh 66.4% sulfuric acid were added thereto. Thereafter, the second hydrolysis reaction was carried out in the same manner as in the same reaction carried out at first. Thus, 304 g of an oily layer and 1390 g of an aqueous layer were obtained. The compositions of the two layers were almost the same as in the second reaction carried out at first.

Under the same conditions as described above, repeated use of the aqueous layer produced in the second reactor was carried out ten times, with 25% of the aqueous layer being added to the first reactor, and 75% of the layer being circulated to the second reactor. But, substantial differences in yield and composition did not appear at any time of repetition.

EXAMPLE 2

The first hydrolysis reaction was carried out in the same manner as in Example 1 except that 131 g (1 mole) of α-methylphenylacetonitrile were used in place of α-isopropyl-p-chlorophenylacetonitrile and that 230 g of 65% sulfuric acid and 35 g of ammonium bisulfate were used. After the reaction was finished, the separated oily layer had the following composition: α-methylphenylacetic acid 70.1%; and α-methylphenylacetamide 29.9%. The yield of the layer was 149 g. The composition of the aqueous layer was as follows: sulfuric acid 32.0%; and ammonium bisulfate 47.0%. The yield of the layer was 245 g. The aqueous layer was cooled to 0° C. to crystallize ammonium bisulfate which was then removed by filtration to recover 69 g of 56.3% sulfuric acid.

This recovered sulfuric acid, 535 g of fresh 66% sulfuric acid and 51 g of ammonium bisulfate were added to the separated oily layer, and the second hydrolysis reaction was carried out in the same manner as in Example 1. After the reaction was finished, 150 g of an oily layer and 653 g of an aqueous layer were separated.

The oily layer was composed of 99.8% of the objective α-methylphenylacetic acid and the aqueous layer was composed of 55.6% of sulfuric acid and 13.0% of ammonium bisulfate.

Next, using 40.5% of the aqueous layer from the second reaction step (composition: sulfuric acid 55.7%, ammonium bisulfate 13.1%), the first hydrolysis reaction was carried out. Thereafter, recovery of sulfuric acid from the aqueous layer obtained in this reaction step, and the second reaction step with this recovered sulfuric acid were further repeated in the same manner as above. As a result, 67 g of 57.2% recovered sulfuric acid and 148 g of an oily layer comprising 99.9% of α-methylphenylacetic acid, were respectively obtained. This result was almost the same as in the first case.

EXAMPLE 3

Hydrolysis was carried out under the same conditions and in the same manner as in Example 1 except that 290 g of α-isopropyl-p-methoxyphenylacetonitrile were used in place of α-isopropyl-p-chlorophenylacetonitrile. Thus, α-isopropyl-p-methoxyphenylacetic acid was obtained in a yield of 98.2%.

EXAMPLE 4

Hydrolysis of α-isopropyl-p-bromophenylacetonitrile with sulfuric acid was carried out in the same manner as in Example 1, except that the amounts of sulfuric acid used in the first and second reaction steps were 1.5 times by mole and 3 times by mole, respectively, based on the nitrile. In the course of reaction, the reaction solution was sampled and the composition of the separated oily layer was examined. The results are shown in the following Table 1. Separately from the above reaction, the hydrolysis was carried out as follows according to the prior art: The whole of sulfuric acid of 3 times by mole based on the nitrile was added at the beginning of the hydrolysis. In the course of reaction, the oily layer was sampled to examine its composition. The results are also shown in the same Table 1.

Table 1

| | Composition | Composition by gas chromatography (%) Time | | | | | | | | | | |
|---|---|---|---|---|---|---|---|---|---|---|---|---|
| | | 4 | 5 | 6 | 7 | 8 | 9 | 10 | 11 | 12 | 13 | 14 |
| Present invention | R—COOH | 78.9 | 86.1 | 89.1 | 97.2 | 99.1 | 99.8 | 100.0 | | | | |
| | R—CONH$_2$ | 21.1 | 13.9 | 10.9 | 2.8 | 0.9 | 0.2 | — | — | | | |
| | | ← First reaction → | | | ← Second reaction → | | | | | | | |
| Prior art | R—COOH | 82.1 | 88.6 | 92.1 | 95.0 | 97.3 | 97.8 | 99.2 | 99.6 | 99.8 | 99.9 | 100.0 |

Table 1-continued

| Compo-sition | Composition by gas chromatography (%) Time | | | | | | | | | | |
|---|---|---|---|---|---|---|---|---|---|---|---|
| | 4 | 5 | 6 | 7 | 8 | 9 | 10 | 11 | 12 | 13 | 14 |
| R—CONH$_2$ | 17.9 | 11.4 | 7.9 | 5.0 | 2.7 | 2.2 | 0.8 | 0.4 | 0.2 | 0.1 | — |

COMPARATIVE EXAMPLES

The following Table 2 shows comparison of the amount of waste water in the process of the present invention (Examples 1 to 3) and the conventional one-step process. Comparative examples 1 to 3 were carried out under reaction conditions (e.g. reaction temperature) as similar to those of the present examples as possible except that they were carried out according to the one-step process.

Table 2

| | Amount of nitrile (g) | Amount of sulfuric acid (g) | | Reaction time (hr) | | Yield % | Amount of waste water (g) |
|---|---|---|---|---|---|---|---|
| | | 1st-step | 2nd-step | 1st-step | 2nd-step | | |
| Example 1 | 280 | 350 | 1400 | 6 | 4 | 99.2 | 320 |
| Comparative Example 1* | 280 | 1310 | | 10 | | 99.0 | 1280 |
| Example 2 | 131 | 265 | 655 | 5 | 4 | 99.8 | 176 |
| Comparative Example 2* | 131 | 905 | | 10 | | 99.8 | 885 |
| Example 3 | 290 | 350 | 1400 | 6 | 4 | 99.5 | 315 |
| Comparative Example 3* | 290 | 1310 | | 10 | | 99.3 | 1270 |

*Respective Reaction conditions of Comparative examples 1 to 3

Required amounts of 65% sulfuric acid and the nitrile compound were charged in the reactor equipped with a condenser, and reaction was carried out at a reaction temperature of 145° to 150° C. for a predetermined time. The obtained reaction mixture was separated into an oily layer and aqueous layer, and the yield of each layer was examined.

The followings are apparent from the above table: According to the present invention, the amount of waste water is about one-fourth to one-fifth of that of the conventional processes although the total amount of sulfuric acid and the molar ratio of sulfuric acid to the nitrile in the second reaction are extremely large, and this means that the process of the present invention is very advantageous in decreasing the COD loading of waste water.

What is claimed is:

1. A process for hydrolyzing a substituted phenylacetonitrile using an acid to produce the corresponding substituted phenyl acetic acid, characterized in that
   (1) the hydrolysis is carried out in at least two steps,
   (2) the acid to be used in a first reaction step is a waste acid produced in a second reaction step and if any, subsequent reaction step(s) thereof in a process carried out previously, and
   (3) the acid to be used in a second reaction step and if any, subsequent reaction step(s) thereof is a waste acid produced in a second reaction step and subsequent reaction step(s) thereof in a process carried out previously, respectively, and a fresh acid, wherein the amount of the acid to be used in the first reaction step is 0.5 to 3 moles per mole of the substituted phenylacetonitrile, the amount of the acid to be used in the second reaction step and the subsequent reaction step(s) if any, is 2 to 8 moles per mole of the substituted phenylacetonitrile, and the hydrolysis is carried out at a temperature of 80° to 250° C.

2. The process according to claim 1, wherein the acid is sulfuric acid.

3. The process according to claim 2, wherein the concentration of the acid in each reaction medium of the first, second and subsequent reaction step(s) if any, is 60 to 70% by weight.

4. The process according to claim 2, wherein the amount of the fresh acid to be used is 1 to 3 moles per mole of the substituted phenylacetonitrile.

5. A process for hydrolyzing a substituted phenylacetonitrile using an acid to produce the corresponding substituted phenylacetic acid, characterized in that
   (1) the hydrolysis is carried out repeatedly batchwise or continuously in at least two steps,
   (2) the first reaction step is carried out using a part of a waste acid produced in a second reaction step in the process carried out previously, and
   the reaction mixture is separated into an oily layer comprising the desired substituted phenylacetic acid and an intermediate substituted phenylacetamide, and an aqueous layer comprising an ammonium salt,
   the oily layer being subjected to the second reaction step, and
   the aqueous layer being taken out of the hydrolysis system without reuse,
   (3) the second reaction step is carried out using a mixture of the remaining part of the waste acid produced in a second reaction step in a process carried out previously with a fresh acid, or a mixture of the remaining part of the waste acid defined above with a part of a waste acid produced in the next subsequent reaction step if any, in a process carried out previously, optionally with a fresh acid, and
   the reaction mixture is separated into an oily layer comprising the desired substituted phenylacetic acid and an aqueous layer comprising a waste acid,
   the oily layer being recovered as a final product or subjected to the subsequent reaction step(s), and the aqueous layer being used at least in each first and second reaction step in the following process to be carried out, and
   (4) each subsequent reaction step if any, is carried out using the remaining part of the waste acid produced in each subsequent reaction step in the process carried out previously and if any, a part of a waste acid produced in each preceding and/or next subsequent reaction step(s) in the process carried out previously, and a fresh acid which is fed to at least one of the subsequent reaction step(s), and (5) the reaction mixture obtained in the final reaction step is separated into an oily layer comprising the desired substituted phenylacetic acid, and an aqueous layer comprising the waste acid, the oily layer being recovered as the final product, and the aqueous layer being reused in the preceding and final reaction steps in the following process to be carried out, wherein the amount of the acid to be used in the first reaction step is 0.5 to 3 moles per mole of the substituted phenylacetonitrile, the amount of the acid to be used in the second reaction step and the subsequent reaction step(s) if any, is 2 to 8 moles per mole of the substituted phenylacetonitrile, and the hydrolysis is carried out at a temperature of 80° to 250° C.

6. The process according to claim 5, wherein the concentration of the acid in each reaction medium of the first, second and subsequent reaction step(s) if any, is 60 to 70% by weight.

7. The process according to claim 5, wherein the amount of the fresh acid to be used is 1 to 3 moles per mole of the substituted phenylacetonitrile.

* * * * *